(12) United States Patent
Elliott et al.

(10) Patent No.: US 6,619,599 B2
(45) Date of Patent: Sep. 16, 2003

(54) INTRAVENOUS (IV) POLE SUPPORTING SYSTEMS

(75) Inventors: Duane Elliott, Indianapolis, IN (US); Dwayne L. Morrow, Flora, IN (US); Larry Rubin, Englewood Cliffs, NJ (US)

(73) Assignee: Emergent Innovations, LLC, Indianapolis, IN (US)

( * ) Notice: Subject to any disclaimer, the term of this patent is extended or adjusted under 35 U.S.C. 154(b) by 0 days.

(21) Appl. No.: 10/087,748

(22) Filed: Mar. 5, 2002

(65) Prior Publication Data

US 2002/0104934 A1 Aug. 8, 2002

Related U.S. Application Data

(63) Continuation-in-part of application No. 09/260,509, filed on Mar. 2, 1999, now Pat. No. 6,375,133.
(60) Provisional application No. 60/076,740, filed on Mar. 4, 1998, and provisional application No. 60/089,851, filed on Jun. 19, 1998.

(51) Int. Cl.$^7$ .............................................. B65G 49/07
(52) U.S. Cl. ..................................... 248/125.8; 5/503.1
(58) Field of Search ............................. 248/129, 125.8, 248/159, 408, 121, 144, 157, 423, 126.1, 207, 318; 5/503.1

(56) References Cited

U.S. PATENT DOCUMENTS

| | | | |
|---|---|---|---|
| 1,199,553 A | | 9/1916 | Hogan |
| 1,900,610 A | * | 3/1933 | Mullins ........................ 108/1 |
| 3,663,972 A | | 5/1972 | Denton |
| 3,709,372 A | | 1/1973 | Alexander |
| 3,835,486 A | | 9/1974 | Benoit et al. |
| 3,951,372 A | | 4/1976 | Casler et al. |
| 4,190,224 A | | 2/1980 | LeBlanc et al. |
| 4,262,872 A | | 4/1981 | Kodet |
| 4,332,378 A | * | 6/1982 | Pryor .......................... 135/67 |
| 4,695,025 A | | 9/1987 | Vaughan |
| 4,725,027 A | * | 2/1988 | Bekanich ................. 248/125.8 |
| 4,807,837 A | | 2/1989 | Gawlik et al. |
| 5,007,604 A | | 4/1991 | Richards |
| 5,135,191 A | * | 8/1992 | Schmuhl .................. 248/125.1 |
| 5,149,036 A | | 9/1992 | Sheehan |
| 5,154,186 A | | 10/1992 | Laurin et al. |
| 5,179,746 A | | 1/1993 | Rogers |
| 5,358,205 A | | 10/1994 | Starkey et al. |
| 5,385,324 A | * | 1/1995 | Pryor et al. .............. 248/228.3 |
| 5,499,721 A | | 3/1996 | Hansen et al. |
| 5,524,667 A | | 6/1996 | Potter |
| 5,582,384 A | | 12/1996 | Schoen |
| 5,619,981 A | | 4/1997 | Breedlove |
| 5,708,577 A | | 1/1998 | Gordon |
| 5,772,162 A | * | 6/1998 | Lin ........................... 248/121 |
| 5,794,897 A | | 8/1998 | Jobin et al. |
| 5,876,016 A | | 3/1999 | Urban et al. |

* cited by examiner

*Primary Examiner*—Ramón O. Ramirez
(74) *Attorney, Agent, or Firm*—Lowe Hauptman Gilman & Berner, LLP

(57) ABSTRACT

An intravenous (IV) support system includes a moveable base and an upright IV pole. The base comprises a lower wheeled plate, an upper plate having a through hole, and an upright elongate tube fastened to the upper and lower plates. The tube is aligned with the through hole of the upper plate to form a passage for the IV pole. A bolt transversely extends through the wall of the tube to form a transverse supporting surface for the IV pole. The IV pole comprises, at a lower end thereof, a pin extending from a flange so that the IV pole may be fitted in a through bore of and supported by a mounting adapter mounted to a patient support frame. The system allows the IV pole to be easily transferable among numerous stand-alone bases and patient support frames, and steadily retained by the bases and mounting adapters mounted to the patient support frames without positive locking mechanisms.

9 Claims, 14 Drawing Sheets

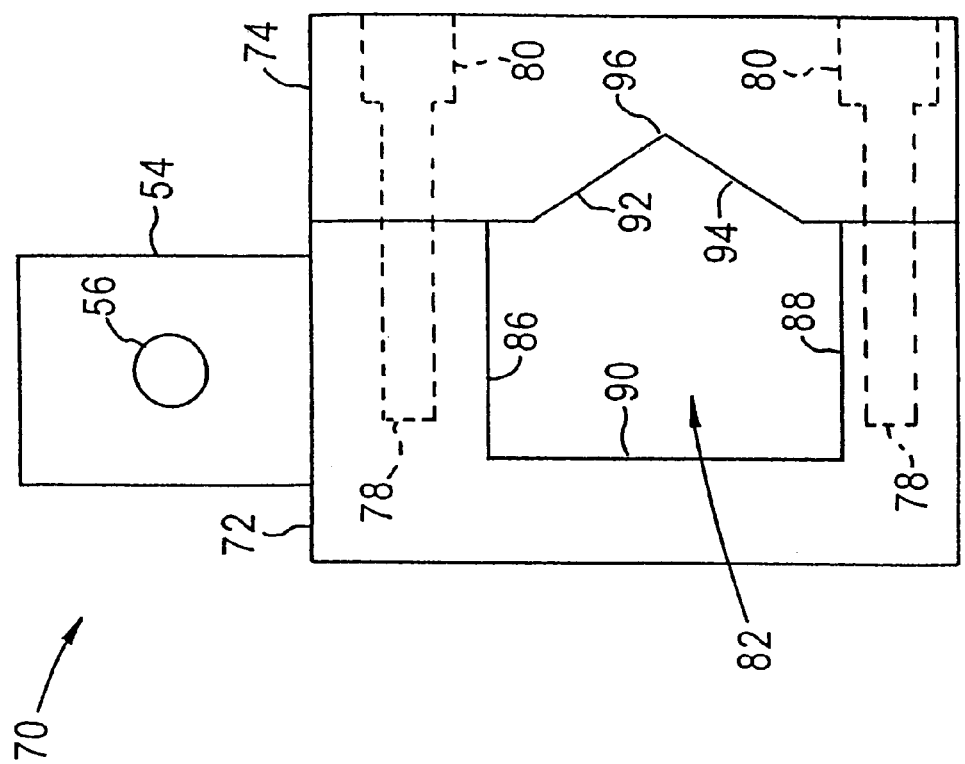
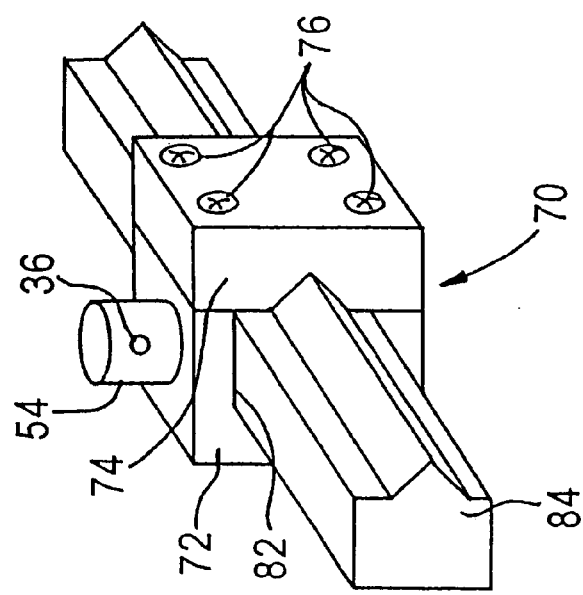
FIG. 3B
FIG. 3A

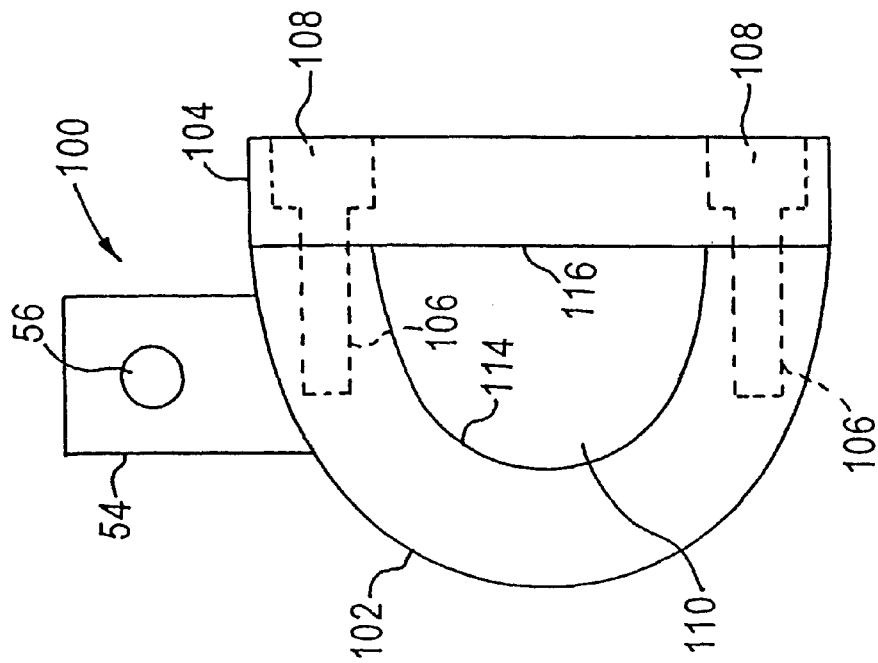
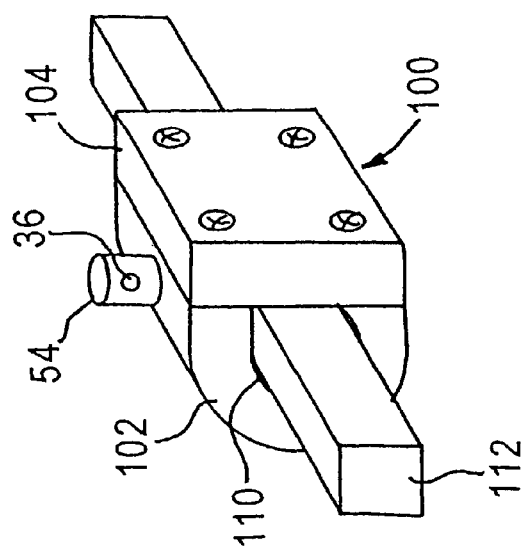
FIG. 4B
FIG. 4A

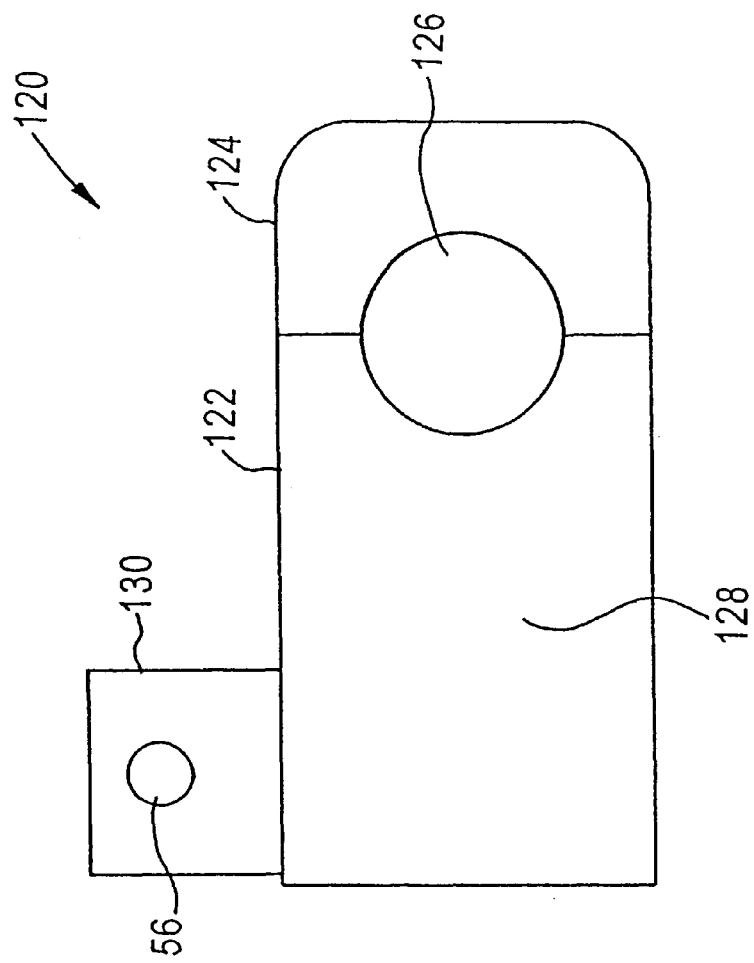
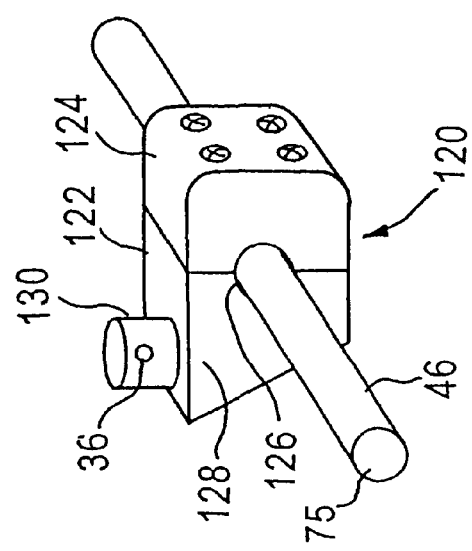
FIG. 5B
FIG. 5A

INTRAVENOUS (IV) POLE SUPPORTING SYSTEMS

RELATED APPLICATION

The present application is a continuation in part of U.S. application Ser. No. 09/260,509, filed Mar. 2, 1999, now U.S. Pat. No. 6,375,133, entitled: "INTRAVENOUS (IV) POLE FOR TRANSPOT WITH MULTIPLE INFUSION DEVICES", which claims priority of U.S. Provisional Application Serial No. 60/076,740, filed Mar. 4, 1998, entitled: "IV POLE FOR TRANSPORT WITH MULTIPLE INFUSION DEVICES", and U.S. Provisional Application Serial No. 60/089,851, filed Jun. 19, 1998, entitled "IV POLE FOR TRANSPORT WITH MULTIPLE INFUSION DEVICES". The disclosures of the application Ser. No. 09/260,509, Nos. 60/076,740, and 60/089,851 are all incorporated by reference herein in their entirety.

FIELD OF THE INVENTION

The present invention relates to the field of medical supports and stands, and more particularly, to an intravenous (IV) support assembly including a plurality of different mounting adapters, each mountable to a patient support frame, and standalone bases which are adapted to support an IV pole for carrying medical equipment.

BACKGROUND OF THE INVENTION

An IV support assembly includes an IV pole for carrying medical equipment thereon and a mounting adapter separable from the IV pole. The mounting adapter is mounted to a patient support frame and can then be used to support the IV pole. The patient support frame can be a bed, stretcher, cot, and the like. As can be appreciated, the support railings or rails on the many different support frames can have many possible configurations, including rectangular, circular, and other cross-sectional configurations. The rails can also include recesses or receptacles used for mounting IV support assemblies to the rails.

In the medical and patient care environments, a need frequently arises to stably and securely mount the IV support assembly to many different patient support frames. For example, when a patient is transferred between first and second patient support frames or beds, an IV support assembly including a mounting adapter secured to the first bed and an IV pole carrying a variety of medical equipment thereon (e.g., plural IV containers and infusion pumps for a patient) must be quickly transferred and mounted to the second bed with minimal disturbance to the equipment. The IV pole itself is preferably transferred directly between the beds without having to move each piece of medical equipment individually to another pole.

Prior art IV mounting adapters and poles are unusable for direct transfer between patient support frames. For instance, the patient support frames often have different patient support rail configurations rendering the same mounting adapter unusable on both patient support frames. Even if appropriately configured mounting adapters are provided for the rails of both patient support frames, a single IV pole will generally be incompatible and thus unusable with both mounting adapters. Use of mounting adapters hung from or otherwise loosely coupled to the patient support frame facilitates IV support assembly transfer between patient support frames, but at the expense of IV pole stability.

An exemplary prior art IV support assembly is disclosed in U.S. Pat. No. 3,709,372. Disclosed is an IV pole 44 supported by a mounting adapter or clamp 50 mounted to a patient support frame or stretcher 10. Mounting adapter 50 disadvantageously requires a pair of perpendicular rails 14,18, instead of a single rail. This arrangement limits the use of mounting adapter 50 to patient support frames having such perpendicularly arranged railing pairs. Because mounting adapter 50 defines through bores or channels of circular cross-section for receiving the rails, the use of mounting adapter 50 is also limited to use with the pair of perpendicular rails of circular cross-sections.

Another prior art IV support assembly is disclosed in U.S. Pat. No. 5,149,036. Disclosed is an IV pole 10 hung or suspended from a rail 27 having planar outer surfaces by a mounting adapter 22. Mounting adapter 22 is a hanging bracket that can be disadvantageously dislodged or decoupled from rail 27 during transport of the bed between locations since the mounting adapter is not secured or clamped to rail 27. Additionally, because mounting adapter 27 is configured to engage the planar surfaces of rail 27, mounting adapter 27 is limited to use with such rails having planar surfaces.

Another prior art IV support assembly is disclosed in U.S. Pat. No. 3,835,486. Disclosed is a patient support frame 10 having a mounting adapter 12 fixed at a predetermined location to patient support frame 10. Disadvantageously, mounting adapter 12 can not be conveniently relocated to another location on support frame 10 or to another patient support frame.

SUMMARY OF THE INVENTION

It is therefore an object of the present invention to provide at least one mounting adapter each configured to be mounted to a different patient support frame configuration.

Another object of the present invention is to provide an IV support assembly including at least one mounting adapter mountable to a single rail of a patient support frame and an IV pole supported by the mounting adapter.

A further object of the present invention is to provide an IV pole efficiently movable from a first mounting adapter on a first patient support frame to a second mounting adapter on a second patient support frame.

Yet another object of the present invention is to provide an adapter kit including a plurality of different mounting adapters each adapted for a different patient support frame configuration and each capable of supporting an IV pole.

Yet a further object of the present invention is to provide an IV support system including a moveable stand-alone base and an upright IV pole to allow the IV pole to be easily placed in and supported by the stand-alone base with no positive locking mechanisms required. The base can be used with or without the IV pole.

These and other objects of the present invention are achieved by an IV support assembly including a mounting adapter and an upright IV pole. The mounting adapter is adapted to be mounted to a single rail of a patient support frame, and includes an insertion member and a locking mechanism. The IV pole is supported by the same mounting adapter, and includes a hollow lower end for receiving the insertion member of the mounting adapter. The IV pole is secured to the insertion member by the locking mechanism of the insertion member. A variety of different mounting adapters each configured for a different rail configuration are available for supporting a common IV pole, so the IV pole is transferable between mounting adapters mounted to different rails.

The foregoing objects of the present invention are also achieved by an IV support assembly usable with a patient support frame having a single rail, the IV support assembly including a mounting adapter adapted to be removably mounted to the single rail, and also including an upright elongate pole member supportable by the mounting adapter.

The foregoing objects of the present invention are also achieved by a mounting adapter for mounting an IV pole to a single rail of a patient support frame, the IV pole having a hollow lower end, the mounting adapter including a separable clamp portion including first and second opposed, mating clamp members together defining a transverse channel for receiving the single rail. The mounting adapter also includes an insertion member extending from the first clamp member for insertion into the hollow lower end of the IV pole, and a locking member for removably securing the IV pole to the insertion member.

The foregoing objects of the present invention are also achieved by a mounting adapter for mounting an intravenous IV pole to a single rail of a patient support frame, the IV pole having a hollow lower end, the single rail having a recess formed in an upper surface thereof, the mounting adapter including an elongate member having upper and lower male portions for respective removable insertion into the hollow lower end of the IV pole and the recess formed in the single rail. The mounting adapter also includes a locking mechanism for securing the hollow lower end of the IV pole to the upper male portion of the elongate member.

The foregoing objects of the present invention are also achieved by an adapter kit for mounting an IV pole to a rail of a patient support frame, the IV pole having a hollow lower end, the rail having at least two configurations, the adapter kit including at least two mounting adapters respectively corresponding to the at least two rail configurations. Each of the at least two mounting adapters includes mounting means for removably mounting the mounting adapter to the rail, an insertion member for removable insertion thereof into the hollow lower end of the IV pole, and a locking mechanism for securing the hollow lower end of the IV pole to the insertion member.

The foregoing objects of the present invention are also achieved by a method for mounting an intravenous (IV) support assembly to first and second patient support frames, the first patient support frame including a single rail having a first configuration, the second patient support frame including a single rail having a second configuration, the IV support assembly including an IV pole for carrying medical equipment thereon and first and second mounting adapters, the first mounting adapter having a configuration corresponding to the first configuration and the second mounting adapter having a configuration corresponding to the second configuration. The method includes the steps of mounting the first mounting adapter to the first patient support frame, supporting the IV pole with the first mounting adapter, mounting the second mounting adapter to the second patient support frame, removing the IV pole from the first mounting adapter, and supporting the IV pole with the second mounting adapter.

The foregoing objects of the present invention are also achieved by an intravenous support assembly, comprising a base and an IV pole. The base comprises at least one base member and an upright elongate pole member being connected to the base member. The upright elongate pole member has an internal hollow space communicated with the outside via an opening formed at an upper end of the upright elongate pole member, and a transverse supporting surface formed in the internal hollow space and spaced downwardly from the upper end. The IV pole has a lower end portion adapted to be telescopically received in the internal hollow space of the upright elongate pole member and fully supported from below by the transverse supporting surface.

In accordance with one aspect of the present invention, the base comprises a lower plate member and an upper plate member having a through hole in alignment with the tube-like upright elongate pole member so as to form a passage for the IV pole. A bolt transversely extends through a circumferential wall of said tube-like upper end portion the an internal hollow space of the upright elongate pole member to define the transverse supporting surface. The base can be used as portable tray when the IV pole is not placed therein.

In accordance with another aspect of the present invention, the IV pole is made, at least in the lower portion thereof, in form of a male portion comprising a pin of a smaller dimension extending downwardly from a flange of a larger dimension so as the IV pole may be supported a mounting adapter which is removably mountable to a patient support frame and has a recess being sized and shaped to receive the pin therein. Preferably, the lower end portion of the IV pole comprises a metal sleeve tightly encapsulating a wooden dowel in which the pin is partially embedded. The IV pole is therefore very light in weight yet mechanically strong.

In accordance with a further aspect of the present invention, a kit comprising a stand-alone moveable base, a mounting adapter and an IV pole is provided. It is also within the scope of the present invention to provide a method of using the kit to quickly move the IV pole from a patient support frame to the stand-alone moveable base and vice versa. The method comprises a) mounting the mounting adapter to a single rail of the patient support frame; b) supporting the IV pole from below by one of the base and the mounting adapter at one of first and second transverse supporting surfaces, respectively; c) removing the IV pole and inserting it into the other of the base and mounting adapter until the lower end of the IV pole rests on and is fully supported from below by the other of the first and second transverse supporting surfaces, respectively. The system and method of the present invention allows the IV pole to be easily transferable among numerous stand-alone bases and patient support frames, and steadily retained by the bases and mounting adapters mounted to the patient support frames without positive locking mechanisms.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description thereof are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout and wherein:

FIG. 3A is a perspective view of a second alternative arrangement of a mounting adapter according to the present invention;

FIG. 3B is an elevational view of the mounting adapter of FIG. 3A;

FIG. 4A is a perspective view of a third alternative arrangement of a mounting adapter according to the present invention;

FIG. 4B is an elevational view of the mounting adapter of FIG. 4A;

FIG. 5A is a perspective view of a fourth alternative arrangement of a mounting adapter according to the present invention;

FIG. 5B is an elevational view of the mounting adapter of FIG. 5A;

BEST MODE FOR CARRYING OUT THE INVENTION

For convenience, the invention will be described in relation to the orientations depicted in FIGS. 1–12 and consequently, terms such as "above" and "below" as used herein are to be construed in the relative sense.

Figure 1:
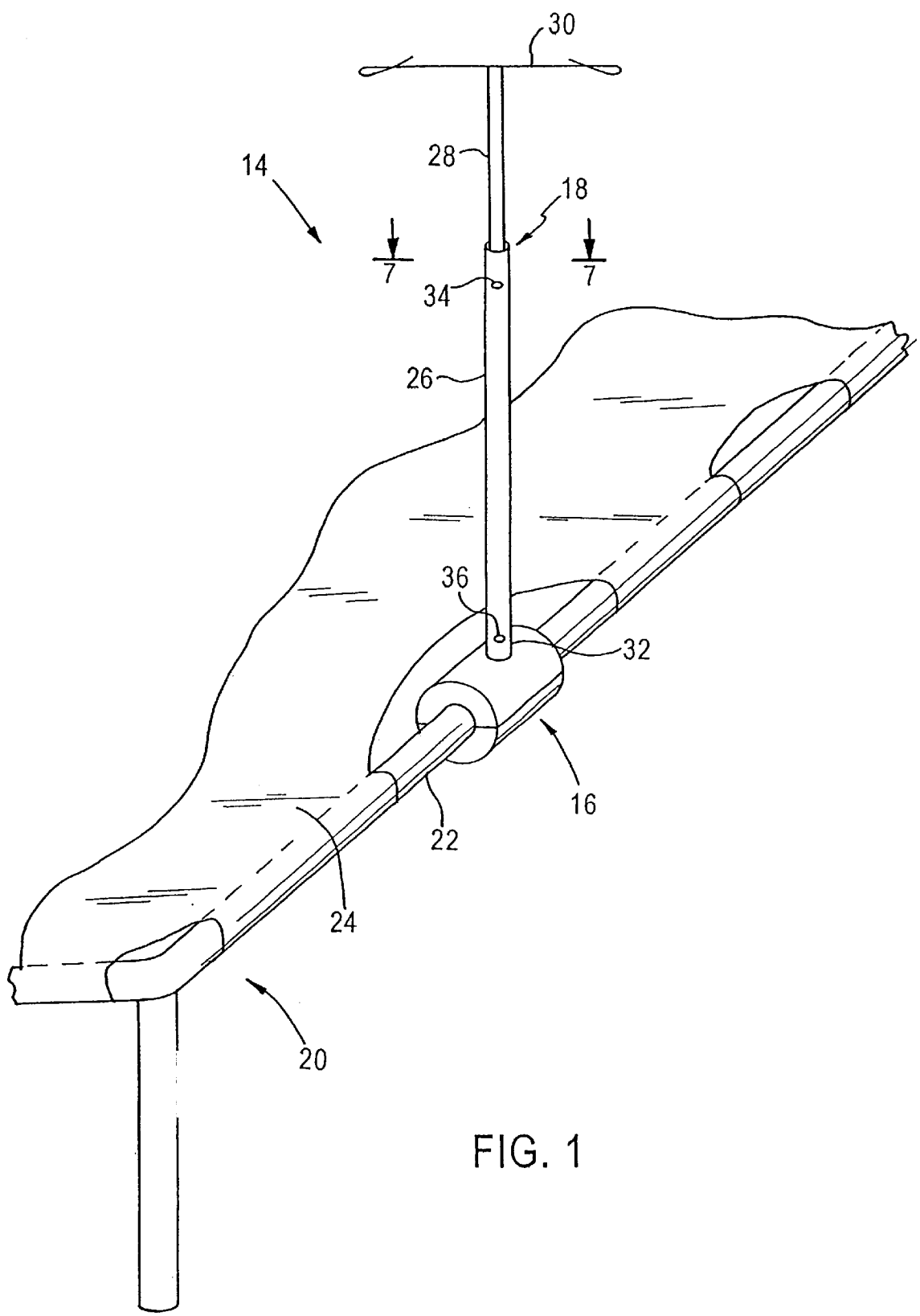
FIG. 1 is a partial perspective view of an embodiment of an IV support assembly including a mounting adapter and an IV pole according to the present invention, the mounting adapter being clamped to a rail of a patient support frame and the IV pole being supported by the mounting adapter.

Referring first to FIG. 1, depicted is an IV support assembly 14 manufactured in accordance with the principles of the present invention. IV support assembly 14 includes a mounting adapter 16 and an IV pole 18. As depicted in FIG. 1, mounting adapter 16 is clamped to a patient support frame 20. Patient support frame 20 is conventional and can be, for example, a hospital bed, stretcher, cot, or the like. Support frame 20 includes an elongate peripheral rail 22 extending around an entire periphery of a patient support web 24. Patient support web 24 can be any conventional web suitable for providing a supporting surface for a patient. Patient support web 24 is attached to peripheral rail 22 using any known technique.

As depicted, IV pole 18 is supported in an upright or vertical position by mounting adapter 16 clamped to peripheral rail 22, as described in detail below. IV pole 18 includes an upright or vertically directed elongate tubular member 26, an upright elongate pole extension 28, and a transverse member 30. Tubular member 26 includes a hollow lower end 32 supported by mounting adapter 16. Pole extension 28 is supported by tubular member 26 and is secured thereto in an extended position by a locking or release pin 34. Transverse member 30 for carrying medical equipment is fixed as by a weld, fastener or other joining means of suitable strength, at a medial portion thereof to an upper end of pole extension 28. Transverse member 30 includes a pair of transversely opposed arms adapted to carry medical equipment including IV bags and the like. The joining means must have sufficient strength to durably withstand torque forces applied thereto resulting from the weight of equipment carried by transverse member 30.

Mounting adapter 16 for supporting IV pole 18 can be clamped to peripheral rail 22 at any location along peripheral rail 22. Mounting adapter 16 can be made of aluminum, stainless steel or other corrosion resistant metal, or of a molded plastic of suitable resiliency and strength to provide a durable and sturdy support for IV pole 18. Advantageously, IV pole 18 is removably secured to the top of mounting adapter 16 by a resiliently biased locking or release pin 36 engaging hollow lower end 32 of IV pole 18. Release pin 36 forms part of a transverse locking mechanism retained by mounting adapter 18. An embodiment of the transverse locking mechanism is depicted in detail in FIG. 9.

The present invention provides a variety of different mounting adapters to accommodate a variety of different configurations of patient support frames. These different mounting adapters collectively form a mounting adapter kit. More specifically, the variety of mounting adapters, i.e., the mounting adapter kit, permits mounting of the IV pole to different rail configurations, for example, to rails having different cross-sectional configurations. Although a variety of different mounting adapters are provided, a common Iv pole is advantageously used with each of the mounting adapters, thus permitting transportability and transferability of the common IV pole between different mounting adapters mounted to different rail configurations.

Figure 2C:
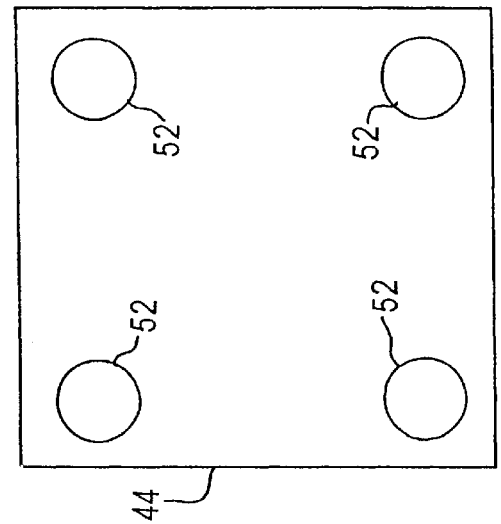
FIG. 2C is a bottom view of the mounting adapter of FIG. 2A.
Figure 2B:
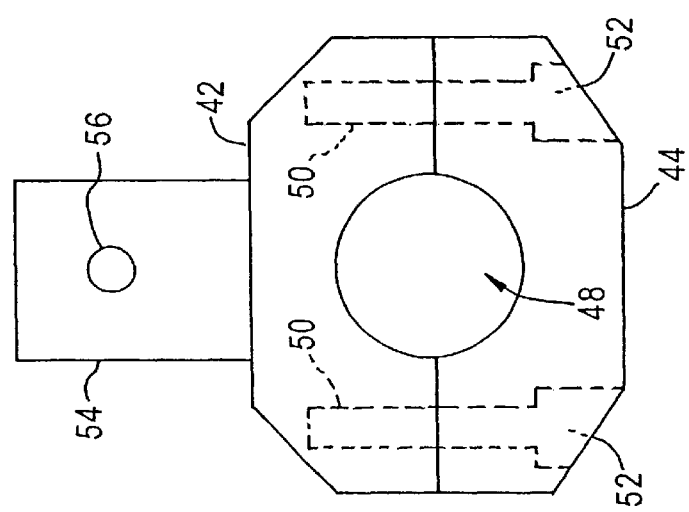
FIG. 2B is an elevational view of the mounting adapter of FIG. 2A.
Figure 2A:
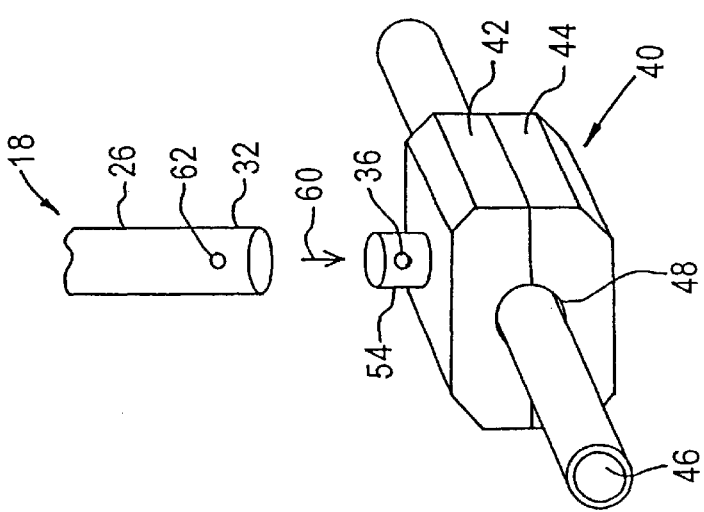
FIG. 2A is a perspective view of a first alternative arrangement of a mounting adapter according to the present invention.

Alternative configurations or arrangements for the mounting adapter are now described. Referring to FIGS. 2A–2C, depicted is a first alternative arrangement of a mounting adapter 40. Mounting adapter 40 includes a first or upper clamp member 42 and a second or lower opposed, clamp member 44. Each of first and second clamp members 42 and 44 includes an inner surface or wall of arcuate, and preferably semi-circular, cross-section along a length thereof, for engaging a corresponding surface of a rail 46 of substantially circular cross-section. First and second clamp members 42 and 44 together define a transverse through bore or channel 48 through mounting adapter 40 for receiving rail 46.

First or upper clamp member 42 is firmly clamped to lower or second clamp member 44, for example, by four threaded bolts (not shown) received by four respective threaded passageways formed through the clamp members. Particularly, a set of four threaded passageways 50 provided in first clamp member 42, and a set of four corresponding threaded passageways 52 provided in clamp member 44, are aligned to form a set of four threaded passageways traversing both clamp members for receiving the bolts. To mount or clamp mounting adapter 40 to rail 46, clamp members 42 and 44 are positioned on opposing sides of rail 46 and bolted together so that their inner surfaces respectively engage opposing surfaces of rail 46; rail 46 is held within channel 48. Preferably, a cross-sectional diameter of rail 46 is slightly larger than a cross-sectional diameter of channel 48 to ensure an interference fit between rail 46 and the inner surfaces of the clamp members. To remove mounting adapter 40 from rail 46, the clamp members are unbolted. In this way, mounting adapter 40 is removably clamped or mounted to single rail 46.

Although as depicted, mounting adapter 40 requires a set of four bolts for assembly, any conventional fastening means can be used to assemble mounting adapter 40 instead of the set of four bolts. For instance, at a side of mounting adapter 40, first and second clamp members 42 and 44 can be pivotally coupled together by a hinge mechanism, while at an opposing side of mounting adapter 40, clamp members 42 and 44 can be bolted together by a pair of bolts. Alternatively, a pair of opposing latching/catch mechanisms can be provided respectively at opposing sides of mounting adapter 40 to clamp together first and second clamp members 42 and 44.

When mounting adapter 40 is mounted to rail 46 as depicted in FIG. 2A, opposing faces of clamp members 42 and 44 meet in a horizontal plane. However, the opposing faces can meet in other planar orientations without sacrificing the mounting stability of the mounting adapter. Also, the opposing faces of clamp members 42 will not actually meet when clamped to an oversized rail, i.e., a rail having a cross-sectional diameter greater than a cross-sectional diameter of transverse channel 48. In such circumstances, mounting adapter 40 can be successfully clamped to the oversized rail so long as the fastening means used to fasten clamp members 42 and 44 together and to the rail can accommodate gaps formed between the opposing faces of clamp member 42 and 44, due to the oversized rail. For instance, when the fastening means is a set of bolts, the bolts must be of a sufficient length to traverse the threaded channels for receiving the bolts and the gap formed between the opposing faces of clamp members 42 and 44.

Insertion member 54 extends from a substantially centralized portion of an upper surface of clamp member 42. Insertion member 54 extends in an upright direction and is substantially vertically aligned with transverse channel 48 (and rail 46 therein) when clamp members 42 and 44 are clamped to rail 46. Preferably, insertion member 54 and upper clamp member 42 are integrally formed, however, insertion member 54 can be bolted or otherwise securely fastened to upper clamp member 42.

Provided in a sidewall of insertion member 54 is an opening 56, as depicted in FIG. 2B. Resiliently biased locking or release pin 36, retained by insertion member 54, extends through opening 56. Release pin 36 is transversely displaceable in first and second opposing directions (toward and away from the sidewall of insertion member 54). Insertion member 54 has a substantially cylindrically shaped body, the diameter of which is such that when insertion member 54 is inserted into hollow lower end 32 of tubular member 26 of IV pole 18, insertion member 54 substantially occupies hollow lower end 32 of tubular member 26.

The assembly and operation of the IV support assembly of the present invention is now described with specific reference to IV pole 18 and mounting adapter 40. First, mounting adapter 40 is mounted to rail 46. Upper and lower clamp members 42 and 44 are fastened together using the set of four threaded bolts or other suitable fastening means previously described, with rail 46 clamped within transverse channel 48 defined between mating clamp members 42 and 44, and with insertion member 54 extending in the upright or vertical direction.

Next, hollow lower end 32 of tubular member 26 of IV pole 18 is moved toward insertion member 54 in the direction of arrow 60 while resiliently biased release pin 36 is depressed to allow passage of hollow lower end 32 over insertion member 54. Formed in a sidewall of hollow lower end 32 of tubular member 26 is an opening 62. When opening 62 is aligned with depressed release pin 36, release pin 36 engages opening 62, i.e., release pin 36 is resiliently displaced in the transverse or horizontal direction to extend through opening 62. In this way, lower end 32 of tubular member 26 of the IV pole is secured to insertion member 54. Since insertion member 54 and IV pole 18 secured thereto are substantially centered above or in vertical alignment with rail 46, a turning moment applied to mounting adapter 40 about rail 46, due to the weight of the IV pole and medical equipment carried thereby, is substantially zero. Advantageously, a very stable IV support assembly results.

To remove or decouple IV pole 18 from clamp member 42 and insertion member 54, release pin 36 is again depressed to disengage release pin 36 from opening 62 and lower end 32 of tubular member 26, thus allowing IV pole 18 to be decoupled from insertion member 54. In this way, IV pole 18 is removably secured to mounting adapter 40. It should be appreciated that since the IV pole is common to all of the mounting adapters, the mechanism used to couple the lower end of the IV pole to each of the mounting adapters, i.e., the insertion member and release pin (as part of the transverse locking mechanism) of the mounting adapter, is shared by each mounting adapter. Advantageously, this permits use of the same IV pole with all of the different mounting adapters.

Referring to FIGS. 3A and 3B, depicted is a second alternative arrangement of a mounting adapter 70. Mounting adapter 70 includes a substantially C-shaped clamp member 72 clamped to an opposing generally parallelepiped-shaped clamp member 74, using a set of four threaded bolts 76 received within threaded and aligned respective channels or passageways 78 and 80 provided in respective clamp members 72 and 74. Any suitable fastening means can be used for clamping the clamp members together, as described for mounting adapter 40. When clamped together, clamp members 72 and 74 define a transverse channel 82 through mounting adapter 70 for receiving a rail 84. Rail 84 includes a plurality of planar faces along a length thereof and has a cross-sectional configuration corresponding to a style of rail on what is known as an Emergency Medical Services (EMS) patient support frame by Stryker Medical Company of Michigan, a division of Stryker Corporation. Transverse channel 82 has a cross-sectional configuration matched to that of rail 84.

Clamp member 72 includes an inner wall or surface along a length thereof for engaging rail 84. The inner surface includes a pair of parallel planar faces 86, 88 and a perpendicular face 90 between planar faces 86 and 88. Opposing clamp member 74 includes an inner wall or surface along a length thereof having a pair of planar faces 92, 94 for engaging rail 84. Planar faces 92 and 94 share a common edge and form an apex 96 along the length of clamp 70 at the common edge. Apex 96 opposes perpendicular face 90 of clamp member 72 when clamp members 72 and 74 are fastened together.

When mounted to rail 84, planar faces 86–94 of mounting clamp 70 respectively engage the plurality of planar faces of rail 84 received in channel 82, since the cross-sectional configurations of channel 82 and rail 84 match. An inner clamp surface area of mounting adapter 70 directly engaging rail 84 is advantageously maximized because of the matched cross-sectional configurations. This results in a stable IV support assembly. Mounting adapter 70 further includes insertion member 54 and release pin 36 for insertion into the lower end of the IV pole, similar to mounting adapter 40.

Referring to FIGS. 4A and 4B, depicted is a third alternative arrangement of a mounting adapter 100. Mounting adapter 100 includes a substantially C-shaped clamp member 102 mated to an opposing, substantially parallelepiped shaped clamp member 104. The two clamp members are clamped together using a set of four bolts received within respective threaded passageways 106 and 108 of respective clamp members 102 and 104. Any suitable fastening means can be used to clamp the clamp members together, as described for mounting adapter 100. When clamped together, a transverse channel or through bore 110 is formed between the clamp members for receiving a rail 112 of substantially rectangular cross-section.

Clamp member 102 includes an inner surface or face 114 of arcuate cross-section along a length thereof, for engaging a surface of rail 112. Clamp member 104 includes an inner planar surface or face 116 for engaging an opposing surface or face of rail 112. When mounted to rail 112, face 114 and planar face 116 engage opposing surfaces of rail 112, and more specifically, planar face 116 engages the planar face of rail 112 thus providing stability against rotation of mount 100 about rail 112, as is similarly achieved by mounting adapter 70. Mounting adapter 100 further includes insertion member 54 and release pin 36 for insertion into the lower end of the IV pole, similar to mounting adapters 40 and 70.

Referring to FIGS. 5A and 5B, depicted is a fourth alternative arrangement of a mounting adapter 120. Mounting adapter 120 is similar to mounting adaptor 40, with an important difference. Mounting adapter 120 includes a first clamp member 122 and a second clamp member 124 fastened together and defining a transverse channel 126 of substantially circular cross-section through mounting adapter 120, for receipt of rail 46. However, unlike mounting adapter 40, first clamp member 122 includes an extension or arm portion 128 extending in a lateral direction away from transverse channel 126 formed between the clamp members. Significantly, insertion member 130 of mounting adaptor 120 extends from a remote end of support arm portion 128 spaced apart from transverse channel 126.

With hollow lower end 32 of tubular member 26 of IV pole 18 coupled to laterally displaced insertion member 130, IV pole 18 is correspondingly laterally displaced with respect to rail 46. This mounting configuration is advantageous in settings where an IV pole provided in substantially vertical alignment with the rail, as with mounting adapters 40, 70 and 100, interferes with either the patient or other medical equipment proximate the rail. Stated otherwise, mounting adaptor 120 advantageously provides a level of clearance from the rail and patient support frame not provided by the other mounting adapters.

Although the clamp members of mounting adapter 120 together define a transverse channel of substantially circular cross-section, alternative embodiments of mounting adaptor 120 including the laterally displaced insertion member, can have other transverse channel configurations, e.g., corresponding to those of mounting adapters 70 and 100. For example, in mounting adaptor 70, C-shaped clamp member 72 can be modified to provide a laterally displaced insertion member similar to insertion member 130 instead of insertion member 54. A similar modification can be made to mounting adaptor 100.

Figure 6A:
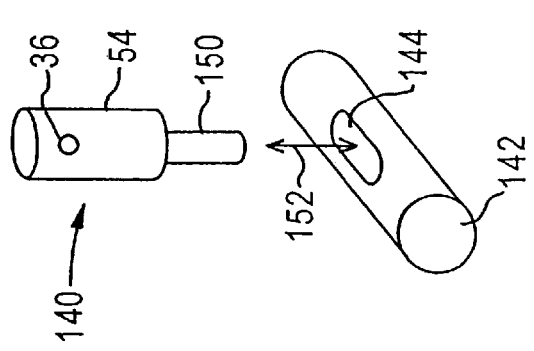
FIG. 6A is a perspective view of a fifth alternative arrangement of a mounting adapter according to the present invention.
Figure 6B:
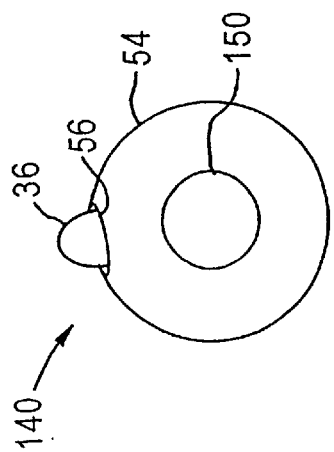
FIG. 6B is a bottom view of the mounting adapter of FIG. 6A.

Referring to FIGS. 6A and 6B, depicted is a sixth alternative arrangement of a mounting adapter 140. Patient support frames often include rails having recesses formed therein, and it is convenient to mount IV poles to the rails using these recesses. As depicted in FIG. 6A, a rail 142 includes a vertically directed recess 144 formed in a top surface thereof. Unlike the previously described mounting adapters, mounting adapter 140 is not clamped to rail 142. Instead, mounting adapter 140 is removably inserted into recess 144 provided in rail 142.

Mounting adapter 140 includes an insertion member 54 for insertion into lower end 26 of tubular member 26 of IV pole 18, similar to the other mounting adaptors. Release pin 36 extends through opening 56 for removably securing lower end 32 of tubular member 26 of the IV pole to mounting adaptor 140. Mounting adapter 140 further includes an anchor pin 150 extending downwardly from a lower surface of insertion member 54. To mount mounting adapter 140 and an IV pole coupled thereto to rail 142, anchor pin 150 is inserted into or received by recess 144 in rail 142. To decouple mounting adapter 140 from rail 142, anchor pin 150 is removed from recess 144 by displacing mounting adapter 140 in an upward vertical direction, e.g., by lifting mounting adapter 140 from recess 144. This removable insertion of anchor pin 150 into recess 144 is represented by arrow 152 in FIG. 6A.

Figure 7:
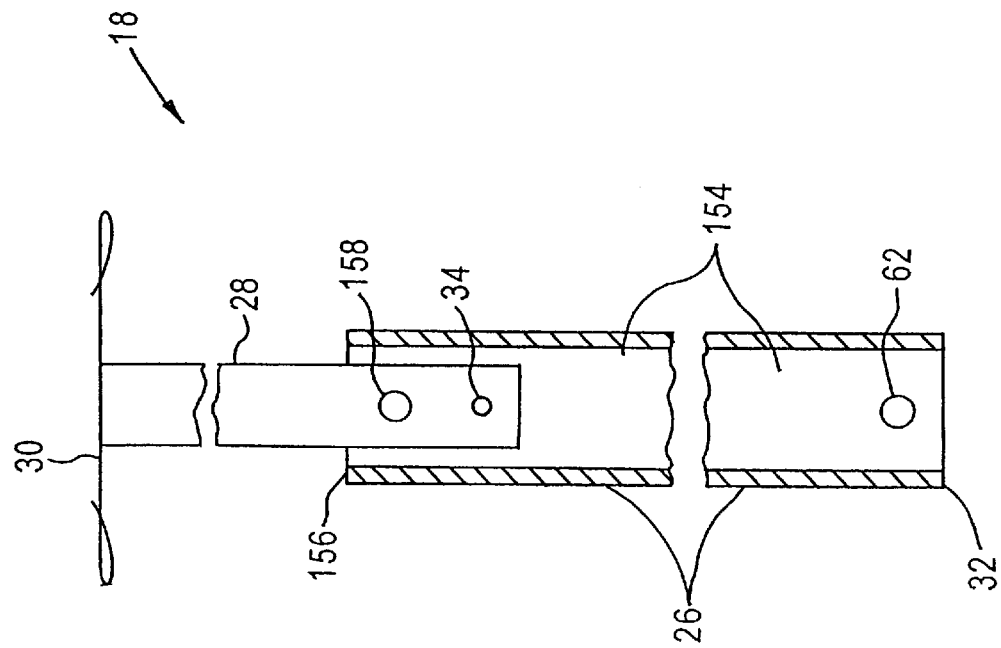
FIG. 7 is a cross sectional view of the IV pole taken through the line 7—7 in FIG. 1.

Referring to FIG. 7, depicted is a cross-sectional view of IV pole 18 of FIG. 1. Tubular member 26, pole extension 28, and transverse member 30 can be made of aluminum, stainless steel or any other corrosion resistant metal having sufficient strength to carry the weight of medical equipment attached to transverse member 30 and tubular member 26. Tubular member 26 includes a through bore 154 between a hollow upper end 156 and hollow lower end 32 thereof. Through bore 154 need not occupy the full length of tubular member 26, for example, a medial portion of tubular member 26 can be solid throughout to strengthen the IV pole. However, tubular member 26 must have hollow upper and lower ends 156 and 32 to respectively receive pole extension 28 and the insertion member used to secure the IV pole to a mounting adapter, as described previously. Formed in the sidewall of lower end 32 and in a sidewall of upper end 156 are respective openings 62 and 158 for engaging respective release pins.

Pole extension 28 is slidingly received within through bore 154 of tubular member 26. Pole extension 28 is displaceable within through bore 154 between an upright extended position for extending a height of IV pole 18, and a retracted or collapsed position wherein a substantially full length of pole extension 28 is retained within through bore 154. Resiliently biased locking pin 34 provided at a lower end of extension 28 within through bore 154 engages, i.e., extends through, opening 158 of tubular member 26 to lock or secure pole extension 28 into the upright extended position, as depicted in FIG. 1. To place pole extension 28 into the collapsed position from the extended, locked position, release pin 34 is depressed to disengage release pin 34 from opening 158. Then, pole extension 28 is displaced (lowered) in the direction of arrow 160.

Figure 8:
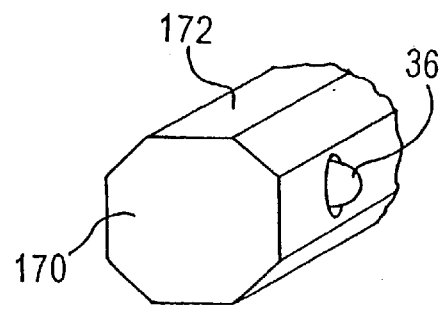
FIG. 8 is a perspective view of an alternative arrangement of an insertion member according to the present invention.

In each of the mounting adapter arrangements previously described, the insertion member forms an upright cylinder or cylindrically shaped stub. This stub is received within hollow lower end 32 of tubular member 26 of the IV pole. FIG. 8 is a perspective view of an alternative arrangement of the insertion member. Insertion member 170 has a hexagonal cross-section, or more generally, insertion member 170 includes an outer surface having at least one planar face 172. Correspondingly, hollow lower end 32 of tubular member 26 of the IV pole includes an inner surface having at least one planar face for engaging planar face(s) 172 of insertion member 170. This advantageously prevents swiveling or rotating of the IV pole about insertion member 170 and thus stabilizes the medical equipment carried by the IV pole. In common with previously described insertion member 54, insertion member 170 includes release pin 36 for removably securing the IV pole to the mounting adaptor.

Figure 9:
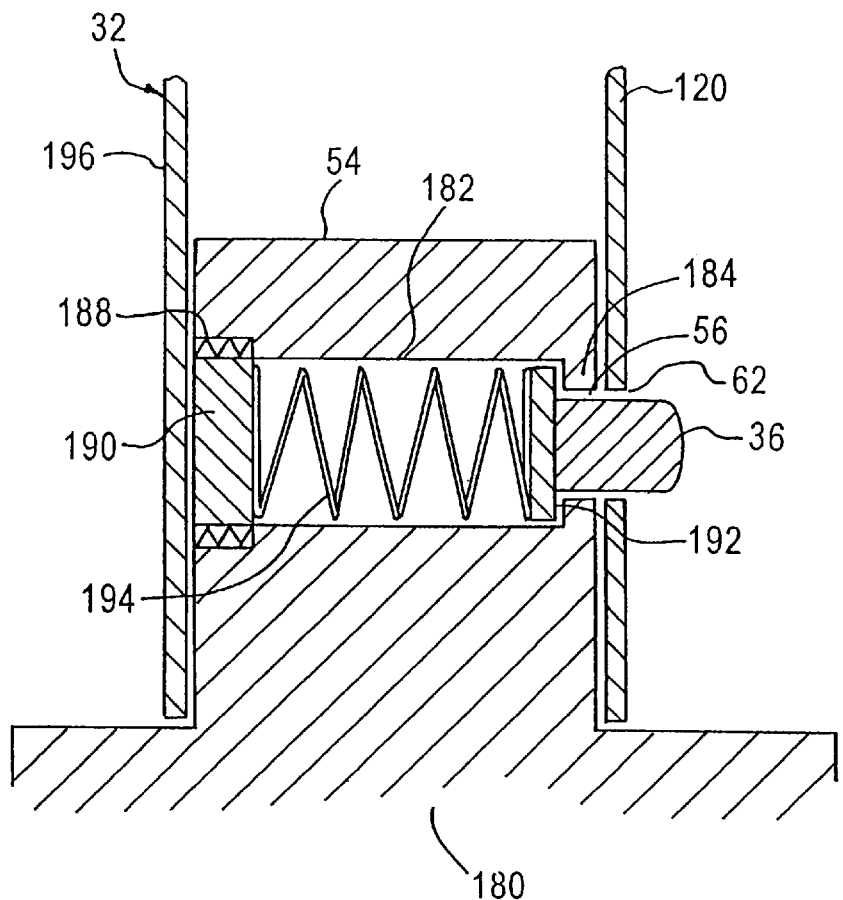
FIG. 9 is a cross-sectional view of an embodiment of a transverse locking mechanism according to the present invention.

Referring to FIG. 9, depicted is an embodiment of the transverse locking mechanism of the present invention for removably securing lower end 32 of tubular member 26 of the IV pole to the insertion member. Insertion member 54 extends from body portion 180 of a mounting adapter. A transverse channel or passageway 182 of substantially cylindrical cross-section is provided through insertion member 54. An annular shoulder or flange 184 is provided at a front end of channel 182 and defines a periphery of opening 56. At a back end of channel 182 is a threaded portion 188. A retaining screw 190 engages threaded portion 188 of transverse channel 182 to seal-off the back end of channel 182. A button end of release pin 36 extends through opening 56 defined by shoulder 184, while a flange 192 of release pin 36 is retained or held captive within channel 182 by shoulder 184. Release pin 36 is resiliently or spring biased by a resilient member or spring 194, held captive and under tension between retaining screw 190 and release pin 36, to extend through opening 156, as depicted. The particular form of resilient member or spring 194 is not important so long as release pin 36 is resiliently biased thereby in accordance with the functionality herein described.

Since the button end of release pin 36 extends through opening 62 formed in a wall 196 of tubular member 26, wall 196 of tubular member 26 of the IV pole is held captive by release pin 36. To release the IV pole from this captive or locked position, release pin 36 is displaced to the left and into channel 182, i.e., depressed, against a biasing force of resilient spring 194. Once release pin 36 has been depressed sufficiently so as to disengage from opening 62 in wall 196, the IV pole can be withdrawn or removed from insertion member 54. In summary, the transverse locking mechanism depicted in FIG. 9 includes a resiliently biased release pin 36 transversely displaceable in first and second opposing directions between a locking position, depicted in FIG. 9, and a release position with respect to opening 62 in wall 196 of tubular member 26 of the IV pole.

In an alternative arrangement, a cotter pin is used to secure the IV pole to the mounting adapter instead of the resiliently biased release pin retained by the insertion member. In operation, the cotter pin is inserted through at least one opening provided in the sidewall of the IV pole, and through a transverse channel formed through the insertion member, similar to the sidewall opening and the channel depicted in FIG. 9.

Figure 10A:
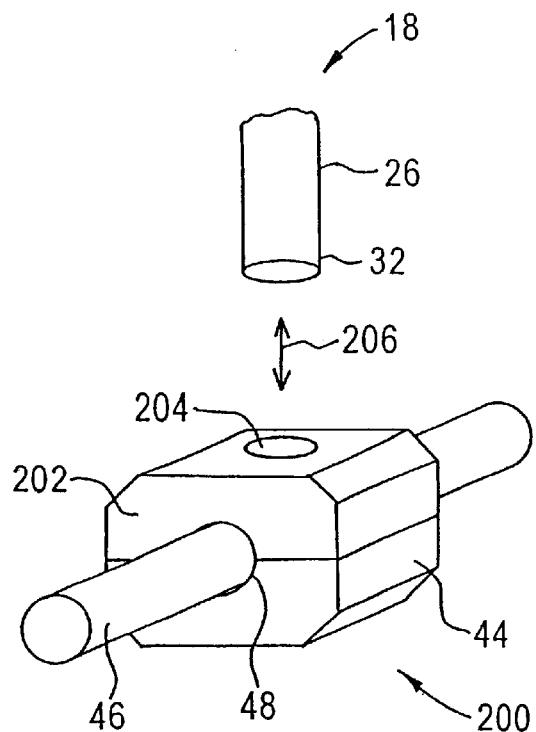
FIG. 10A is perspective view of another alternative arrangement of a mounting adapter according to the present invention.
Figure 10B:
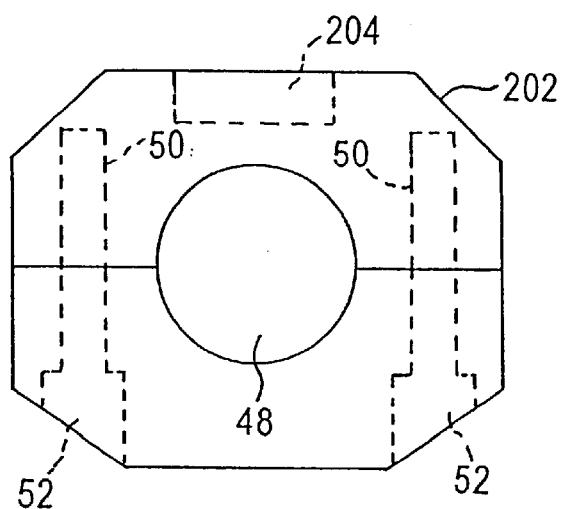
FIG. 10B is an elevational view of the mounting adapter of FIG. 10A.

In the preceding description, the various mounting adapters, 40, 70, 100, and 120 include insertion members 54 or 130 for securing the IV pole to a respective mounting adapter. However, depicted in FIGS. 10A and 10B is an alternative arrangement of a mounting adapter 200 having a recess, i.e., receptacle, instead of the insertion member, for receiving the lower end of the IV pole and for supporting the IV pole. As depicted in FIGS. 10A and 10B, first or upper clamp member 202 includes a vertically directed recess 204 in an upper surface of clamp member 202. Recess 204 is sized to receive lower end 32 of tubular member 26 of the IV pole therein. First clamp member 202 is clamped to opposing clamp member 44 and to rail 46 in a similar manner as was described for mounting adapter 40.

To couple IV pole 18 to mounting adapter 200, lower end 32 of tubular member 26 is inserted into recess 204. With lower end 32 retained within recess 204, mounting adapter 200 supports IV pole 18. To remove IV pole 18 from mounting adapter 200, tubular member 26 is lifted, i.e., displaced in an upward vertical direction, to disengage lower end 32 from recess 204. The removable insertion of lower end 32 into recess 204 is depicted by arrow 206. It should be appreciated that with this arrangement, lower end 32 of tubular member 26 need not be hollow, i.e., lower end 32 can be solid throughout, since no insertion member 54 is inserted therein. Additionally, to secure lower end 32 to mounting adapter 202, a transverse locking mechanism can be added to or retained by first clamp member 202, the transverse locking mechanism adapted to engage the sidewall of lower end 32 when lower end 32 is retained within recess 204.

Figure 11A:
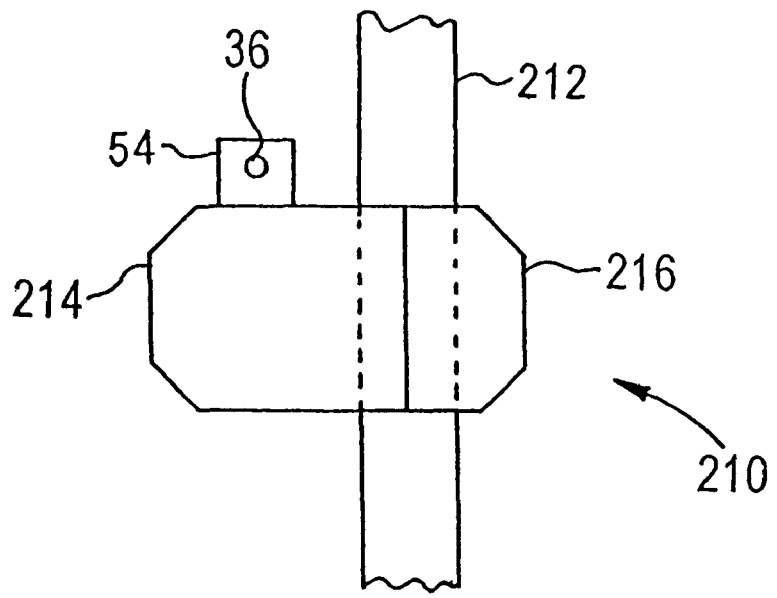
FIG. 11A is an elevational view of another alternative arrangement of a mounting adapter according to the present invention.
Figure 11B:
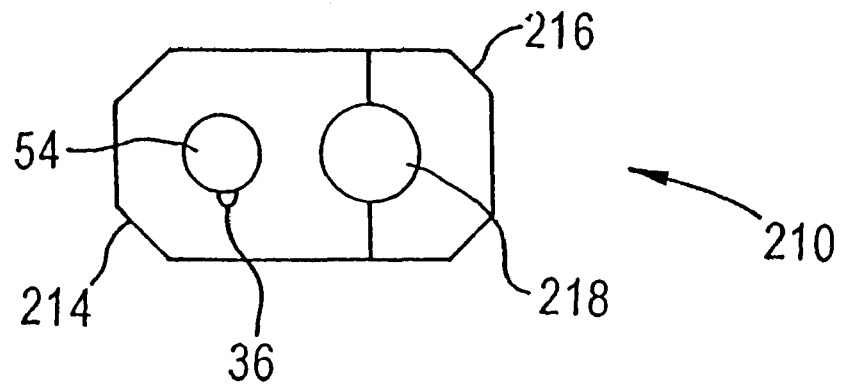
FIG. 11B is a top view of the mounting adapter of FIG. 11A.

In the preceding Figures, the various mounting adapters, 40, 70, 100, and 120 are depicted as being mounted to respective single rails extending in a first direction, i.e. the transverse direction, while the respective insertion members of the mounting adapters extend in the upright or vertical direction, i.e., perpendicular to the direction of the single rails. However, depicted in FIGS. 11A and 11B is an alternative arrangement of a mounting adapter 210 for mounting to a single rail 212 extending in the vertical direction, wherein single rail 212 and insertion member 54 are parallel, i.e., both extend in the vertical direction when mounting adapter 210 is mounted to rail 212.

Mounting adapter 210 includes a first clamp member 214 and a second clamp member 216 clamped together and to rail 212 in a similar manner as was described previously for mounting adapter 40. Each of first and second clamp members 214 and 216 includes an inner surface or wall, of substantially semi-circular cross-section, along a length thereof, for engaging a corresponding surface of rail 212 of circular cross-section. First and second clamp members 214 and 216 together define a through bore or channel 218 in mounting adapter 210. Through bore 218 extends in a direction parallel to the direction of insertion member 54. In this way, mounting adapter 212 is mountable to upright or vertical rails and can support an upright IV pole when mounted thereto. It should be appreciated that a recess (e.g. recess 204 of FIG. 10A), instead of insertion member 54, can be provided in first clamp member 214 to retain the IV pole.

Figure 12B:
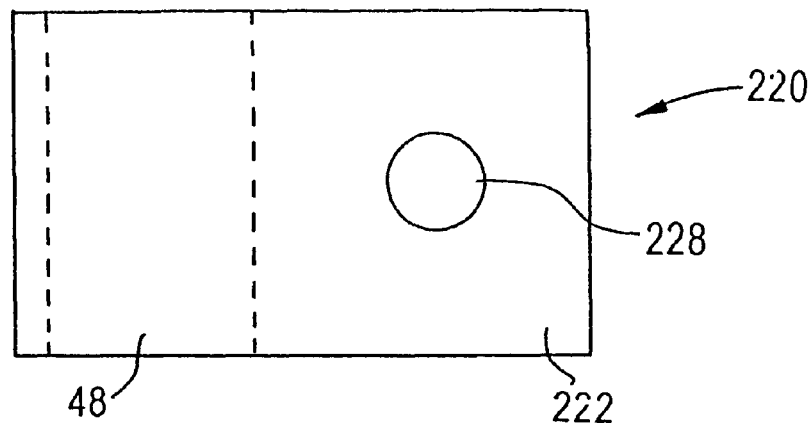
FIG. 12B is a top view of the mounting adapter of FIG. 12A.
Figure 12A:
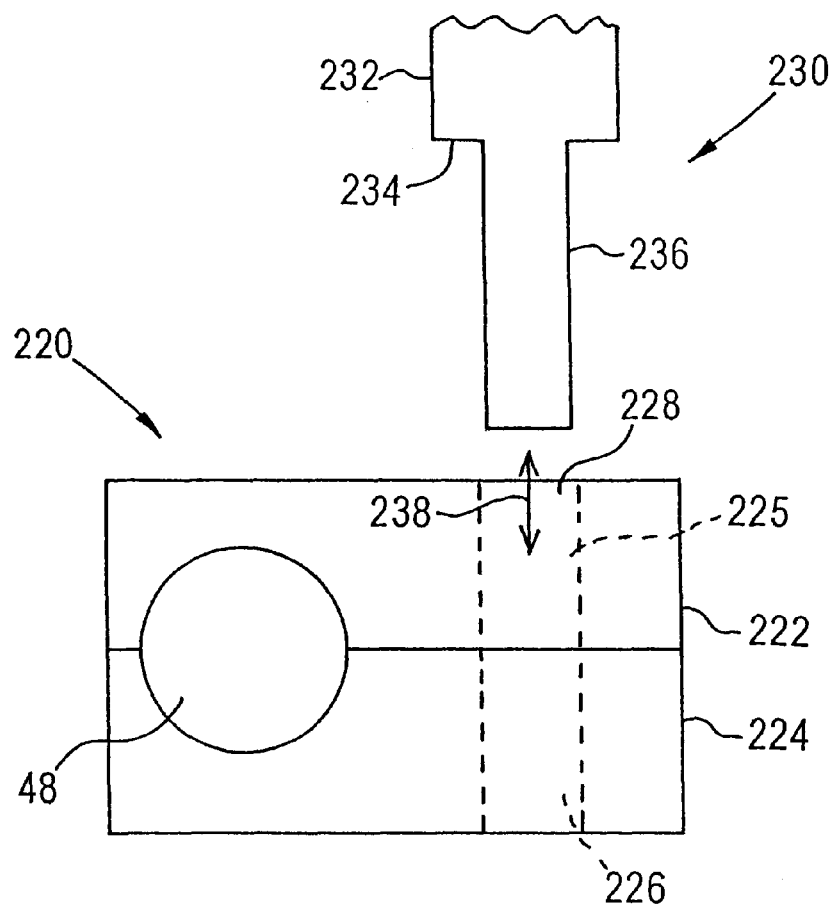
FIG. 12A is an elevational view of another alternative arrangement of a mounting adapter according to the present invention.

FIGS. 12A and 12B are illustrations of another alternative arrangement of a mounting adapter 220. Mounting adapter 220 includes a first or upper clamp member 222 and an opposed second or lower clamp member 224. Each of first and second clamp members 222 and 224 includes an inner surface or wall of arcuate, and preferably semicircular, cross-section along a length thereof, for engaging a corresponding surface of a single rail 46 (FIG. 2A) of substantially circular cross-section. First and second clamp members 222 and 224 together define a transverse through bore or channel 48 through mounting adapter 220 for receiving rail 46.

First clamp member 222 includes a vertical through bore 225, and second clamp member 224 includes a vertical through bore 226 having substantially the same diameter as through bore 225 and in substantial vertical alignment with through bore and 225. Through bores 225 and 226 together define a vertical through bore 228 through mounting adapter 220 when clamp members 222 and 224 are clamped together and to rail 46, using any suitable fastening means.

Mounting adapter 220 is adapted for use with an IV pole having a lower end 230 as depicted in FIG. 12A. The IV pole includes a lower end 232 of an upright tubular member of the IV pole. Lower end 232 terminates in a narrowed shoulder portion 234, and includes an insertion pin 236 depending vertically from shoulder portion 234. Insertion pin 236 has a diameter less than a diameter of lower end 232 of the tubular member and is centered along an axis of the tubular member. Insertion pin 236 can be integrally formed with lower end 232 of the tubular member, or alternatively, insertion pin 236 can be a separate member removably coupled to tubular member 232, e.g., similar to mounting adapter 140 of FIGS. 6A and 6B.

To couple the IV pole having lower end 232 to mounting adapter 220, insertion pin 236 is inserted into through bore 228 so that shoulder portion 234 of lower end 232 rests upon an opposing (upper) surface of first clamp member 222. In this way, mounting adapter 220 supports the IV pole. To remove the IV pole from mounting adapter 220, the IV pole is lifted to disengage insertion pin 236 from through bore 228. The removable insertion of insertion pin 236 into through bore 228 is depicted by arrow 238.

In another embodiment of the present invention, IV pole 18 is mobilized using a wheeled trolley. In this embodiment, lower end 32 of tubular member 26 is removably mounted to the wheeled trolley. The wheeled trolley includes a base having a lower and an upper surface. A plurality of spaced wheels, e.g., four or six wheels, are attached to the bottom surface of the base and permit the base to roll freely over a floor surface. The upper surface of the base includes either insertion member 54 or recess 204 therein to support, i.e., removably secure or retain, respectively, lower end 32 of tubular member 26 of the IV pole. When IV pole 18 is supported by the upper surface of the wheeled trolley, IV pole 18 can be wheeled across the floor surface, thus permitting transportability of IV pole 18. In an alternative arrangement of the wheeled trolley, the upper surface of the base includes an upright tubular member having a through bore therein. The through bore is sized to receive a length of tubular member 26 of IV pole 18 therein. Tubular member 26 is secured within the through bore by a transverse locking mechanism. In addition to the transverse locking mechanisms previously described, a transverse screw can be used to secure tubular member 26 within the through bore.

A mounting adapter kit of the present invention comprises at least two different mounting adapters previously described. For instance, a mounting adapter kit comprises mounting adapter 40 together with mounting adapter 70, or alternatively, mounting adapter 40 together with mounting adapter 100. Other adapter kits comprising alternative permutations and combinations of mounting adapters can be constructed as the need arises.

The present invention supports transfer of an IV pole between two or more different mounting adapters mounted to two or more respective patient support frames having different single rail configurations, e.g. between two beds having rails with different cross-sectional configurations. For example, assume that 1) mounted to rail 46 of circular cross-section of a first patient support frame is mounting adapter 40,
2) mounted to rail 112 or 84, of rectangular cross-section or of "Stryker" configuration, of a second patient support frame is mounting adapter 70 or 100, and
3) secured to mounting adapter 40 mounted to the first patient support frame is IV pole 18 carrying medical equipment thereon.

Then, transfer of IV pole 18 from the first patient support frame to the second patient support frame is effected efficiently by 1) removing IV pole 18 from mounting adapter 40 mounted to the first patient support frame, and
2) securing IV pole 18 to mounting adapter 70 or 100 mounted to the second patient support frame.

Figure 13:
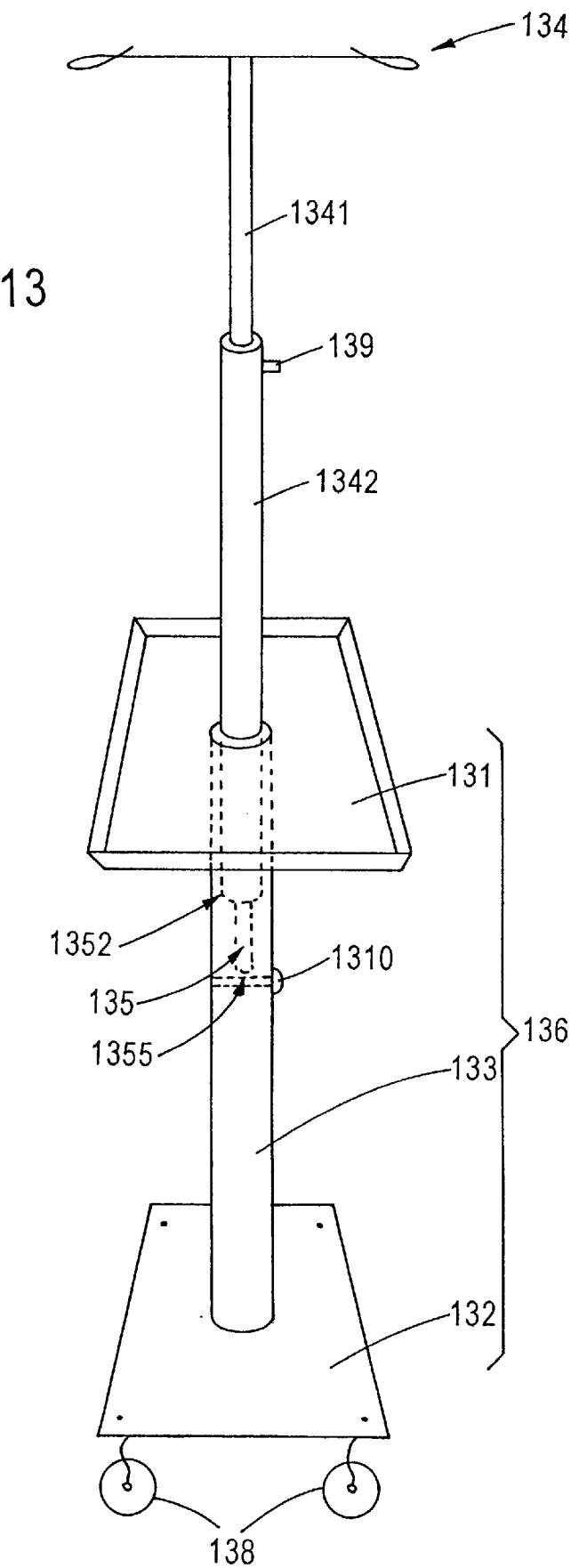
FIG. 13 is a perspective view of a system comprising an IV pole and a movable base, according to the present invention.
Figure 14A:
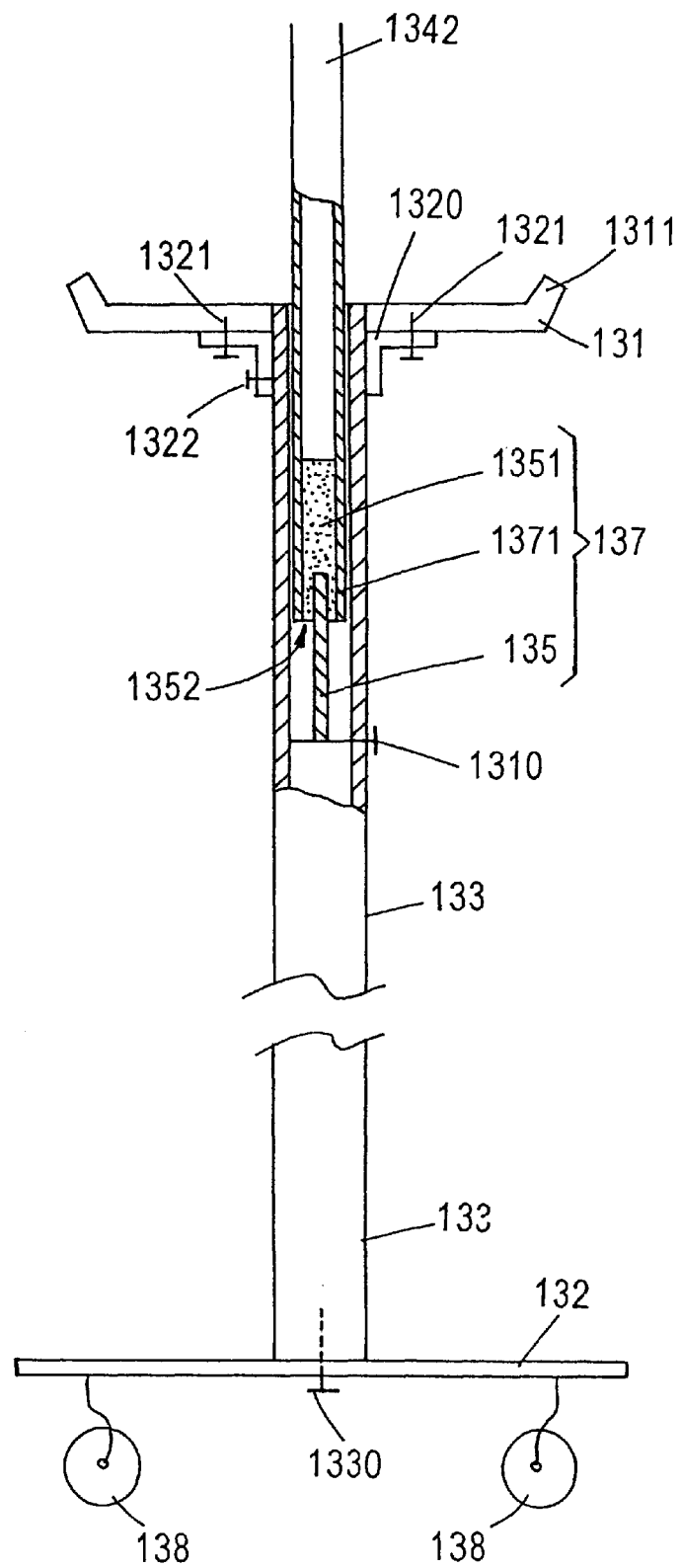
FIGS. 14A and 14B are front, partially sectional views of the system shown in FIG. 13 when the IV pole is received in and removed from the base, respectively.
Figure 14B:
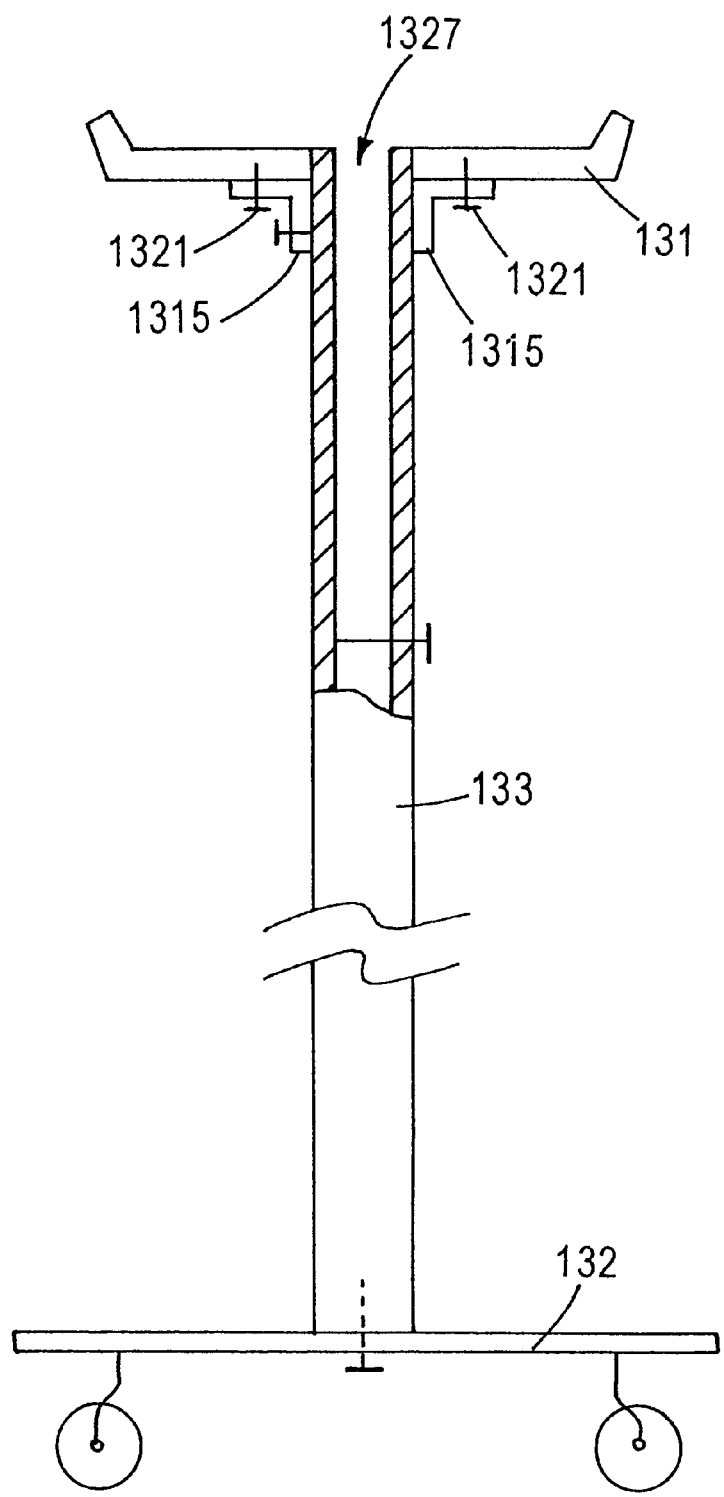

Reference will be now made to FIGS. 13–14 where another embodiment of the present invention is illustrated. FIG. 13 is a perspective view of an IV supporting system comprising IV pole 134 and movable stand-alone base 136, while FIGS. 14A and 14B are front, partially sectional views of the system shown in FIG. 13 when IV pole 134 is placed in and removed from base 136, respectively.

Base 136 includes upper plate 131, lower plate 132 and pole member 133 fastened to upper plate 131 and lower plate 132 at upper and lower ends thereof, respectively. Preferably, lower plate 132 is a steel panel and pole member 133 is a metal tube made of e.g. aluminum. However, other arrangements are not excluded and, as will be described herein below, any pole member having at least a hollow end, e.g. an upper end, can be used as pole member 133 in base 136 of the present invention. Although, it is within the scope of the present invention to manufacture upper plate 131 from any materials of suitable mechanical strength, e.g. steel, it is preferable to make upper plate 131 from plastic to lower the center of gravity of base 136 as well as of the whole system when IV pole 134 is placed in base 136. Upper plate 131 and lower plate 132 are preferably sized so as to prevent medical equipment, e.g. IV bags, hung on the IV pole from hitting walls, or at least lessen potential damages caused by such impacts, during transportation of the IV system e.g. in hospital hallways.

Figure 15:
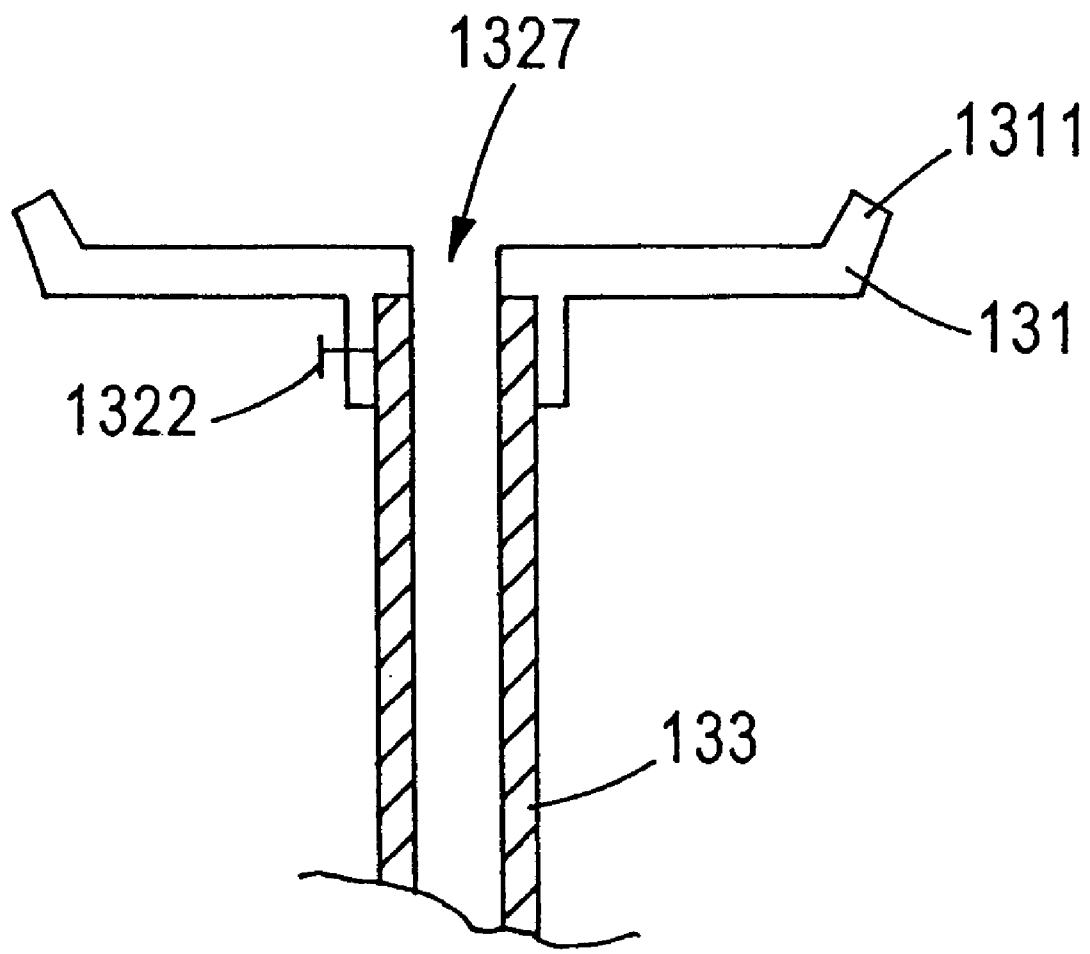
FIG. 15 is a sectional view showing an alternative arrangement for the upper tray of the base illustrated in FIGS. 14A and 14B.

Upper plate 131 has a through hole (best seen in FIG. 14B) in a central region thereof. The through hole is in alignment with tube-like upper end of pole member 133 to provide passage for IV pole 134. The through hole may be sized to circumferentially fit over the uppermost end of pole member 133, as can be seen in FIG. 14B, or cover it, as can be seen in FIG. 15. Upper plate 131 is preferably fastened to pole member 133 by fastening member 1315 and bolt 1322 extending through fastening member 1315 and making contact with the outer surface of pole member 133. Fastening member 1315 may be two or more discrete L-shaped elements arranged opposing each other diametrically of pole member 133. Preferably, fastening member 1315 is a sleeve circumferentially fitted over the upper end portion of pole member 133. Fastening member 1315 may be made separate from upper plate 131 and fastened thereto by bolts 1321, as can be seen in FIG. 14B, or made integral with upper plate 131, as can be seen in FIG. 15.

Lower plate 132 is fastened to pole member 133 by e.g. bolt 1330 extending upwardly from the underside of lower plate 132. A number, e.g. 4, of wheels or castors 138 are mounted to the underside of lower plate 132 to render base 136 moveable. In the embodiment shown in FIGS. 13–14 four castors are used (only two of them shown). However, it is within the scope of the present invention to provide base 136 with more or less wheels to suit a particular requirement.

An advantage of base 136 of the present invention is that in case no IV poles are placed in the base, as depicted in FIG. 14B, upper plate 131 of base 136 can be used as a portable tray carrying various instruments needed for medical or minor surgical procedures e.g. sterile surgical or exam instruments, syringes etc. The portable tray can also hold instruments and IVs for use in veterinary surgery suites. Additional equipment can be placed on lower plate 132 as well. When no IV poles are placed in base 136, a hole 1327 (FIG. 14B) exists in the central region of upper plate 131. The hole can be left as is or covered by an optional cover (not shown) to prevent unwanted objects from falling in the inside of pole member 133.

IV pole 134, except for lower end portion 137 thereof, is substantially identical to IV pole 18 described in the foregoing description of FIG. 1. More particularly, IV pole 134 includes an upright or vertically directed elongate tubular member 1342, an optional upright elongate pole extension 1341, and a transverse member for carrying medical equipment. Pole extension 1341 is supported by tubular member 1342 and is secured thereto in an extended position by a locking or release pin 139. That is, pole extension 1341 is telescopically retractable into and extendable from tubular member 1342. When pole extension 1341 is extended from tubular member 1342, extra hydrostatic pressure may be obtained. Preferably, IV pole 134 is a tube or a series of telescopically fitted tubes made of metal e.g. aluminum. However, other arrangements are not excluded as long as IV pole 134 is light weight and has a sufficient mechanical strength.

Reference will be now made to lower end portion 137 which serves as a main difference between IV poles 134 and 18. As best seen in FIG. 14A, lower end portion 137 comprises tubular member 1371 tightly encapsulating dowel 1351 in which pin 135 is partially embedded. A substantial part of pin 135 (FIG. 13) is of a smaller cross sectional dimension (e.g. diameter) and extends downwardly from an end flange 1352 of a larger cross sectional dimension (e.g. diameter).

This configuration is similar to the one shown in FIG. 12A in which lower end 232 of an IV pole has shoulder portion 234 and insertion pin 236 depending vertically from shoulder portion 234. Therefore IV pole 134 is usable with mounting adapter 220 shown in FIG. 12 by inserting pin 135 into through bore 228 so that end flange 1352 of lower end portion 137 rests upon an opposing (upper) surface of first clamp member 222. It is not excluded that mounting adapter 220 has a recess instead of through bore 228 in which case IV pole 134 might be supported by mounting adapter 220 when distal end 1355 of pin 135 comes to rest on a bottom of the recess (not shown).

The configuration of pin 135 is also suitable for IV pole 134 to be directly placed in recess or through bore 144 formed in rail 142 of the patient support frame shown in FIGS. 6A and 6B. In this instance, mounting adapter 140 will not be necessary.

In the embodiment illustrated in FIG. 14A, distal end 1355 of pin 135 rests on and is supported from below by a transverse supporting surface i.e. bolt 1310 transversely extending through a wall of pole member 133 although other arrangements are not excluded. Bolt 1310 may be permanently screwed into the wall of pole member 133.

It should be now clear that IV pole 134 is usable with numerous supporting elements such as mounting adapter 220, rail 142 and stand-alone moveable base 136. The IV pole can be quickly moved among the above supporting elements in a manner substantially as described above.

The pin configuration of FIG. 14A is advantageous because IV pole 134 is extremely light weight yet mechanically strong. In a preferred embodiment, tubular member 1371 is made of aluminum, dowel 1351 is made of wood and pin 135 is made of steel. The finished product is as light as 1.5 lbs and can hold as many as three IV pump of 13 lbs each.

It is important to have the outer dimension of at least the lower end portion of IV pole 134 and inner dimension of at least the upper end portion of pole member 133 properly sized so as to provided snug fitting therebetween. It is also important that a sufficient length of IV pole 134 be received inside pole member 133. The above two factors ensure that IV pole 134 in most cases will not be falling off base 136 after being placed therein. Thus, IV pole 134 can be steadily retained by pole member 133 without the need for additional locking mechanisms.

In a preferred embodiment, upper plate 131 and lower plate 132 are 16×16×⅛" steel plates, pole member 133 and IV pole 134 are 35" aluminum tubes having inner and outer diameters, respectively, of about 1". Wooden dowel 1351 is 4" long. Bolt 1310 is located about 6" below upper plate 131 and pin 135 is sized so that at least 3" of tubular member 1371 is received inside pole member 133. Pin 135 is ½" in diameter. IV pole 134 is about 24" long when pole extension 1341 is retracted. Castors are 5" wheels.

It will be readily seen by one of ordinary skill in the art that the present invention fulfills all of the objects set forth above. After reading the foregoing specification, one of ordinary skill will be able to affect various changes, substitutions of equivalents and various other aspects of the invention as broadly disclosed herein. It is therefore intended that the protection granted hereon be limited only by the definition contained in the appended claims and equivalents thereof.

What is claimed is:

1. An intravenous support assembly, comprising:
    a base comprising at least one base member and a first upright elongate pole member being connected to said at least one base member, said first upright elongate pole member having
        an internal hollow space communicated with an outside of said first upright elongate pole member via an opening formed at an upper end thereof, and
        a transverse supporting surface formed in the internal hollow space and spaced downwardly from the upper end of said first upright elongate pole member; and
    a second upright elongate pole member having a lower end portion adapted to be telescopically received in the internal hollow space of said first upright elongate pole member and fully supported from below by the transverse supporting surface;
    wherein
        the lower end portion of said second upright elongate pole member snugly fits in the internal hollow space of said first upright elongate pole member: and at least one sixth of an entire length of said second upright elongate pole member is receivable in the internal hollow space, whereby said second upright elongate pole member is steadily retained by said first upright elongate pole member without a positive locking mechanism.

2. An intravenous support assembly, comprising:

a base comprising at least one base member and a first upright elongate pole member being connected to said at least one base member, said first upright elongate pole member having an internal hollow space communicated with an outside of said first upright elongate pole member via an opening formed at an upper end thereof, and a transverse supporting surface formed in the internal hollow space and spaced downwardly from the upper end of said first upright elongate pole member; and a second upright elongate pole member having a lower end portion adapted to be telescopically received in the internal hollow space of said first upright elongate pole member and fully supported from below by the transverse supporting surface;

wherein the lower end portion of said second upright elongate pole member is configured as a male portion comprising a pin of a smaller dimension extending downwardly from a flange of a larger dimension, a distal end of said pin coming to rest on the transverse supporting surface when said second upright elongate pole member is inserted into the internal hollow space of said first upright elongate pole member.

3. The assembly of claim 2, further comprising a mounting adapter adapted to be removably mounted to and carried by a single rail of a patient support frame on which a patient is carried, said mounting adapter having a bore extending downwardly from an upper surface thereof, the bore being sized and shaped to receive said pin therein while the upper surface of said mounting adapter being adapted to form a stop for said flange.

4. The assembly of claim 2, wherein the lower end portion of said second upright elongate pole member comprises a sleeve tightly encapsulating a dowel in which said pin is partially embedded.

5. A base for use in an IV system to provide support for an IV pole, said base comprising:

a lower plate member;

an upper plate member having a through hole in a central region thereof; and an upright elongate pole member having upper and lower end portions connected to said upper and lower plate members, respectively;

wherein the upper end portion of said upright elongate pole member is made tube-like and positioned in alignment with the through hole of said upper plate member so as to form a passage for the IV pole;

said upright elongate pole member further comprises a transverse supporting surface formed in said tube-like upper end portion thereof and spaced downwardly from said upper plate member so as to form a stop and support for the IV pole; and said upper plate member comprises a sleeve at a underside thereof, the sleeve circumferentially fits over said tube-like upper end portion and is fastened thereto by a bolt extending through the sleeve and making contact with said tube-like upper end portion.

6. An IV pole suitable for use with an IV support base member having a cavity sized and shaped to partially receive the IV pole therein, said IV pole comprising:

an upper end portion having at least a holding member for holding and carrying external medical equipment; and a lower end portion configured as a male portion comprising a pin of a smaller dimension extending downwardly from a flange of a larger dimension, the lower end portion comprising a metal sleeve tightly encapsulating a wooden dowel in which said pin is partially embedded.

7. The IV pole of claim 6, wherein said upper end portion is telescopically retractable into and extendable from said lower end portion.

8. A method of moving an IV pole between a patient support frame including a single rail and a stand-alone movable IV supporting base having an internal upright passage and a first transverse supporting surface formed in the passage, said method comprising the steps of:

mounting a mounting adapter to the single rail of the patient support frame, said mounting adapter having a bore and a second transverse supporting surface;

inserting the IV pole into one of the passage of the IV supporting base and the bore of the mounting adapter until a lower end of the IV pole rests on and is fully supported from below by the respective one of the first and second transverse supporting surfaces;

removing the IV pole from said one of the passage and the bore; and inserting the IV pole into the other of the passage and the bore until the lower end thereof rests on and is fully supported from below by the other of the first and second transverse supporting surfaces, respectively.

9. The method of claim 8, wherein the lower end of the IV pole has distinct first and second supported portions spaced longitudinally, and when the IV pole is inserted into the passage or the bore, the first or second supported portions comes to rest on the first or second transverse supporting surfaces, respectively.

* * * * *